United States Patent
Ryser et al.

(10) Patent No.: US 7,730,766 B2
(45) Date of Patent: Jun. 8, 2010

(54) GAS VISCOSITY SENSOR

(75) Inventors: Peter Ryser, Morges (CH); Sigfrid Straessler, St-Saphorin (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 313 days.

(21) Appl. No.: 11/886,597

(22) PCT Filed: Mar. 30, 2006

(86) PCT No.: PCT/IB2006/000730
§ 371 (c)(1),
(2), (4) Date: Sep. 18, 2007

(87) PCT Pub. No.: WO2006/103542
PCT Pub. Date: Oct. 5, 2006

(65) Prior Publication Data
US 2009/0229351 A1    Sep. 17, 2009

(30) Foreign Application Priority Data
Mar. 31, 2005    (EP)  .................................. 05405277

(51) Int. Cl.
*G01N 9/32* (2006.01)
*G01N 11/10* (2006.01)
(52) U.S. Cl. .................... 73/30.04; 73/24.05; 73/30.01; 73/31.05; 73/54.01
(58) Field of Classification Search ................ 73/24.05, 73/30.01, 30.04, 31.05, 54.01–54.43
See application file for complete search history.

(56) References Cited

U.S. PATENT DOCUMENTS

| | | | | |
|---|---|---|---|---|
| 4,166,381 A | * | 9/1979 | Woo | 73/54.25 |
| 4,357,834 A | * | 11/1982 | Kimura | 73/708 |
| 4,604,898 A | * | 8/1986 | Gohin et al. | 73/701 |
| 4,750,351 A | * | 6/1988 | Ball | 73/54.04 |
| 4,926,682 A | | 5/1990 | Holm-Kennedy et al. | |
| 5,477,726 A | * | 12/1995 | Stabinger et al. | 73/32 A |
| 5,537,860 A | * | 7/1996 | Haertl | 73/54.14 |
| 5,668,303 A | * | 9/1997 | Giesler et al. | 73/24.06 |
| 6,178,811 B1 | * | 1/2001 | Bonne et al. | 73/54.04 |
| 6,872,071 B1 | | 3/2005 | Durst | |
| 2004/0115068 A1 | * | 6/2004 | Hansen et al. | 417/379 |
| 2005/0223783 A1 | * | 10/2005 | Spivak | 73/54.14 |
| 2007/0220976 A1 | * | 9/2007 | Ewerlin | 73/579 |

FOREIGN PATENT DOCUMENTS

WO    WO 01/96832 A1    12/2001

* cited by examiner

*Primary Examiner*—David A. Rogers
(74) *Attorney, Agent, or Firm*—Baker & Daniels LLP

(57) ABSTRACT

A gas viscosity sensor comprises a signal processing circuit and a sensor element, including a gas pressure generating system and a differential pressure measuring system in fluid communication therewith, the differential pressure measuring system comprising a measuring chamber (14) bounded by a thin membrane (28), an inlet-outlet channel or orifice interconnecting the measuring chamber to a source of gas for which the viscosity is to be determined, the inlet-outlet channel or orifice having dimensions adapted to provide resistance to the outflow and inflow of gas in the measuring chamber, and a membrane displacement sensor (32) adapted to measure a time dependent displacement of the membrane due to pressure variations in the measuring cavity.

22 Claims, 5 Drawing Sheets

GAS VISCOSITY SENSOR

The present invention relates to a sensor for measuring the viscosity of a gas.

There are many applications in which the measurement of the viscosity of a gas is useful. One important application concerns the determination of properties of combustible gases, in particular natural gas, in order to optimize combustion thereof. The composition of natural gas may vary quite significantly depending on the origin of the natural gas, which in turn has a direct effect on the optimum amount of air (oxygen) needed for optimal combustion in a given system, which may also depend on many other properties, such as the pressure, temperature, rate of combustion. More specifically, combustion of natural gases is controlled by certain values that define the combustion of natural gas and that are known as the lambda value $\lambda$ and the Wobbe index ($W_o$). It is moreover known that there is a correlation between the Wobbe index and the dynamic viscosity of the gas, and it is therefore possible to determine the Wobbe index by measuring the gas viscosity, as explained in more detail here below.

The stoichiometric air requirement of a fuel is the amount of dry air required to completely combust one mole of fuel gas. Air is only 20.9% oxygen. For complete combustion to occur, the air/fuel (A/F) ratio for every mole of a hydrocarbon fuel represented by the formula CxHy is given by $$(A/F)_{stoich} = 4.785\left(x + \frac{1}{4}y\right) \quad (1)$$

Table 1 below shows selected hydrocarbons and their corresponding air requirements

TABLE 1

AIR TO FUEL RATIO REQUIREMENT FOR THE COMBUSTION OF SELECTED ALKANES

| component i | $(A/F)_{stoich,i}$ |
|---|---|
| methane | 9.57 |
| gasoline | 14.7 |
| ethane | 16.75 |
| propane | 23.93 |
| butane | 31.1 |
| pentane | 38.28 |

For a mixture of gases with the composition $\{x_i\}$ the air to fuel ratio can be calculated from $$(A/F)_{stoich} = \sum_i (A/F)_{stoich,i} \quad (2)$$

The lambda value $\lambda$ is defined by $$\lambda = \frac{(A/F)_{actual}}{(A/F)_{stoich}}. \quad (3)$$

In combustion the fuel and the volume of air flow, $\dot{V}$ depends on the density $\rho$ via the relation $$\dot{V} = C\sqrt{\frac{2\Delta p}{\rho}} \quad (4)$$

where $\Delta p$ is the pressure drop across the inlet orifice and C is some constant. Because of the dependence on the density one has to introduce the combustion air requirement index CARI by the definition:

$$CARI = (A/F)_{stoich}\sqrt{\frac{\rho_{air}}{\rho_{fuel}}}. \quad (5)$$

If the CARI is known one can adjust the air flow to obtain the required value for $\lambda$. The Wobbe index $W_o$ determines the required air flow and is defined as $$W = H_0\sqrt{\frac{\rho_{air}}{\rho_{fuel}}}. \quad (6)$$

where $H_0$ is the caloric value

It turns out that for the range of composition in natural gas one finds that the Wobbe index and CARI are related via $$W = 97.732\ CARI - 29.692. \quad (7)$$

For various reasons the requirement to obtain the correct value for $\lambda$ is usually discussed in the literature via the Wobbe index and not the CARI.

Choosing the correct value for lambda depends on the application, as discussed in the following examples.

Stoichiometric burn engines

Stoichiometric burn engines are used for light-duty application because they can be equipped with a three-way catalyst exhaust for post-combustion treatment technology to meet light-duty vehicle exhaust emissions standards.

Lean-burn engines

Lean-burn engines are designed to operate at an air/fuel ratio with more air than required to completely burn the fuel, which is referred to as lean fuel conditions. Medium and heavy-duty engines are usually designed as lean-burn engines because they are more fuel-efficient and produce lower combustion temperatures than stoichiometric burn combustion. This engine technology has been used to meet applicable exhaust emission standards without the use of after-treatment technology. Excess air both ensures that all the fuel is burned and dilutes the combustion products to reduce the combustion gas temperature. The lower combustion temperatures minimize emissions without after-treatment.

Boilers

Combustion in boilers incorporates a modest amount of excess air—about 10 to 20% beyond what is needed to burn the fuel completely. This is necessary in order to avoid the unintentional generation of flammable and toxic products of incomplete combustion, including carbon monoxide and hydrogen.

From the above discussion it follows that in the presence of a variable fuel (e.g. natural gas) it is necessary to measure the Wobbe index in order control the combustion. In principle the Wobbe index can be measured before, during or after the combustion. Methods which measure during the combustion are based on the ionization current of the flame emission. After combustion the air/fuel ratio can be determined by oxygen sensor. These methods are however complex and costly to implement, especially in relation to mass applications.

It has been shown that the measurement of the viscosity of natural gas represents the Wobbe factor with sufficient accuracy, as shown in the known graph in FIG. 1.

In U.S. Pat. No. 6,872,071, a device for adjusting the air-fuel ratio, based on the measurement of gas viscosity in order to determine the Wobbe index, is generally described.

In WO 01/96832, a sensor for determining the viscosity of a gas, in particular to regulate the air-fuel ratio, is described. The sensor has a cavity with a driver membrane in the form of a speaker to vary the cavity volume, and a sensor membrane in the form of a microphone to measure the dynamic pressure in the cavity. The cavity being connected to the gaseous environment through a resistive orifice. The dynamic pressure response is a function of the gas viscosity. A drawback of the device described in the aforementioned document that is fairly costly to manufacture, particularly in mass production, and is difficult to produce as a particularly compact, reliable and accurate sensor.

Another gas viscosity sensor is described in U.S. Pat. No. 4,926,682. The sensor comprises a cavity and a resistive orifice, one side of the cavity being bounded by a membrane that is displaced in order to vary the volume within the cavity, by means of a capacitive effect. The capacitor is formed by conductive layers on the membrane and on a surface of the cavity opposite the membrane. On application of an electrical charge, the membrane is displaced, whereby the rate of displacement is affected by the viscosity of the gas in the cavity, and thus affects the voltage response of the capacitor. A drawback of this sensor is the relatively high cost in manufacturing the capacitor, in particular the various stacked layers of different compositions, and the difficulty of obtaining reliable and precise viscosity measurements from reading of the capacitor response.

An object of the invention is to provide a reliable, compact and performant sensor for measuring the viscosity of a gas and parameters correlated to the gas viscosity, such as density, or the Wobbe index (of a combustible gas).

It is advantageous to provide a gas viscosity sensor that is robust and that may be employed in chemically aggressive environments.

It is advantageous to provide a gas viscosity sensor that is cost-effective to manufacture and install, and that remains reliable over time.

It is advantageous to provide a gas viscosity sensor that is robust and accurate, while being compact and easy to install and to operate.

Objects of this invention have been achieved by providing the gas viscosity sensor according to claim 1.

Disclosed herein is a gas viscosity sensor comprising a signal processing circuit and a sensor element including a gas pressure generating system and a differential pressure measuring system in fluid communication therewith, the differential pressure measuring system comprising a measuring chamber bounded by a thin membrane, a membrane displacement sensor adapted to measure a time dependent displacement of the membrane due to pressure variations in the measuring cavity, correlated by the signal processing circuit to a parameter dependent on gas viscosity, and an inlet-outlet channel or orifice interconnecting the measuring chamber to a source of gas for which the viscosity is to be determined, the inlet-outlet channel or orifice having dimensions adapted to provide resistance to the outflow and inflow of gas in the measuring chamber.

The pressure generating system advantageously includes an expansion chamber in which the pressure of the gas is varied, separate from the measuring chamber.

The expansion chamber preferably comprises a heating element arranged to heat gas in the expansion chamber.

The measuring chamber, thin membrane, inlet-outlet channel or orifice, and an expansion chamber of the pressure generating system may advantageously be integrally formed in a ceramic substrate with LTCC (Low Temperature Cofired Ceramic) tape technology.

The cavities and orifices of the ceramic element may be formed with a sacrificial layer, such as carbon black.

The heating element may advantageously comprise a conductive resistor track on a membrane bounding a cavity of the expansion chamber.

The membrane displacement sensor may advantageously comprise a heat sensitive resistor positioned on the thin membrane. Another heat sensitive resistor is preferably positioned on a substrate of the sensor element, off the thin membrane, to act as a reference for the heat sensitive resistor of the membrane displacement sensor.

The measuring chamber and expansion chamber may be arranged adjacent each other in substantially the same plane and in fluid communication via a channel formed in the substrate. Other configurations, such as stacking or assembly of separate chambers may also be used.

The signal processing circuit may comprise a memory storing a set of values related to time dependent membrane displacement profiles for comparison with the time dependent displacement of the membrane.

In a preferred mode of operation, the signal processing circuit is adapted to switch on the heating element for a duration T1 corresponding to a heating cycle, and to switch off the heating element for a duration T2 corresponding to a cooling cycle. The membrane displacement sensor measures the time dependent displacement of the membrane over the cooling cycle and matches or compares such profile with values stored in a memory of the signal processing circuit.

In a particular embodiment, the sensor can be adapted to measure the Wobbe index $W_o$ of a combustible gas by correlating the Wobbe index with a dynamic viscosity value obtained from measurement of the time dependent membrane displacement.

Further objects and advantageous features of the invention will be apparent from the claims and following detailed description and drawings, in which:

Figure 2:
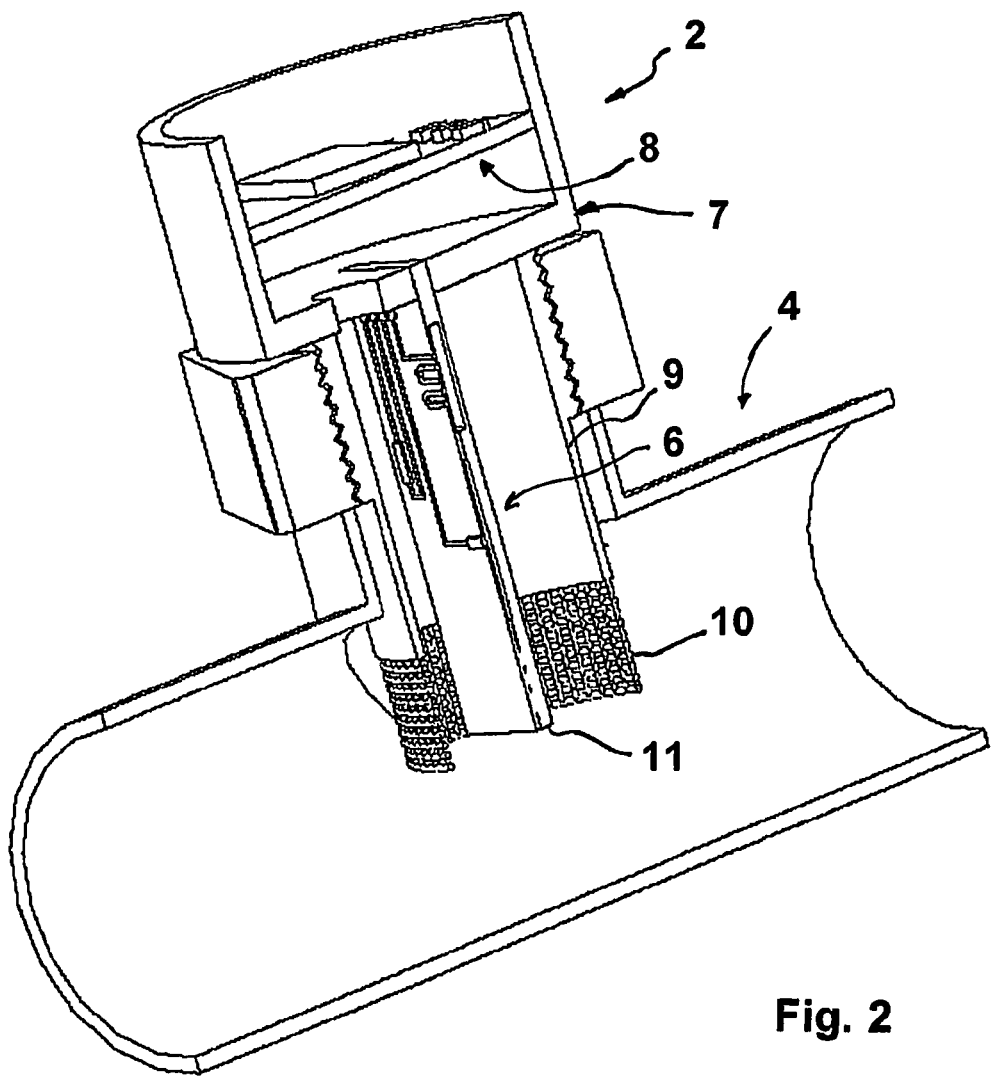
FIG. 2 is a respective cross-sectional view of a gas viscosity sensor according to this invention, mounted on a gas conduit.

Referring first to FIG. 2, a gas viscosity sensor 2 is shown, mounted on a T-section of a gas supply conduit 4, through which flows a gas, the density or viscosity of which is to be measured by the sensor. In the embodiment described here-after, reference is made to the measurement of the viscosity of a natural gas. The sensor according to the invention however can be used for measurement of viscosity of many other types of gases and is in no way limited to the viscosity measurement of a combustible gas. As discussed above, the viscosity measurement of natural gas, which may be correlated with the Wobbe index, is particularly useful in applications for controlling the air/fuel mixture for optimal combustion.

The sensor 2 comprises a sensor element 6 and a signal processing circuit 8 mounted in a housing 7. The signal processing circuit 8 is connected to the sensor element 6 for supplying power and for processing the input and output signals of the sensor element. The sensor housing 7 comprises a shell portion 9 surrounding the sensor element 6. The shell portion has an extremity 10 that is perforated, or made of mesh, and that provides a protective shell around the gas inlet extremity 11 of the sensor element, while allowing gas flowing to access the sensor element.

Figure 3:
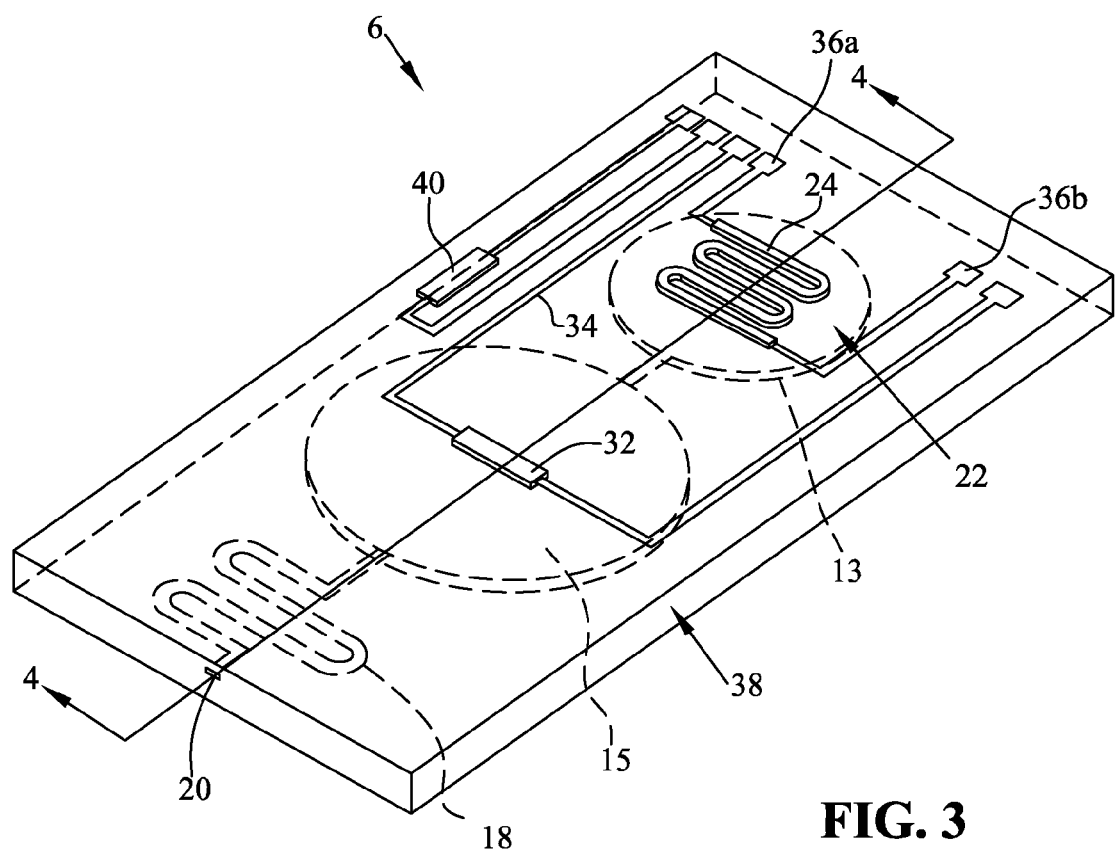
FIG. 3 is a perspective view of a sensor element according to the invention.
Figure 4:
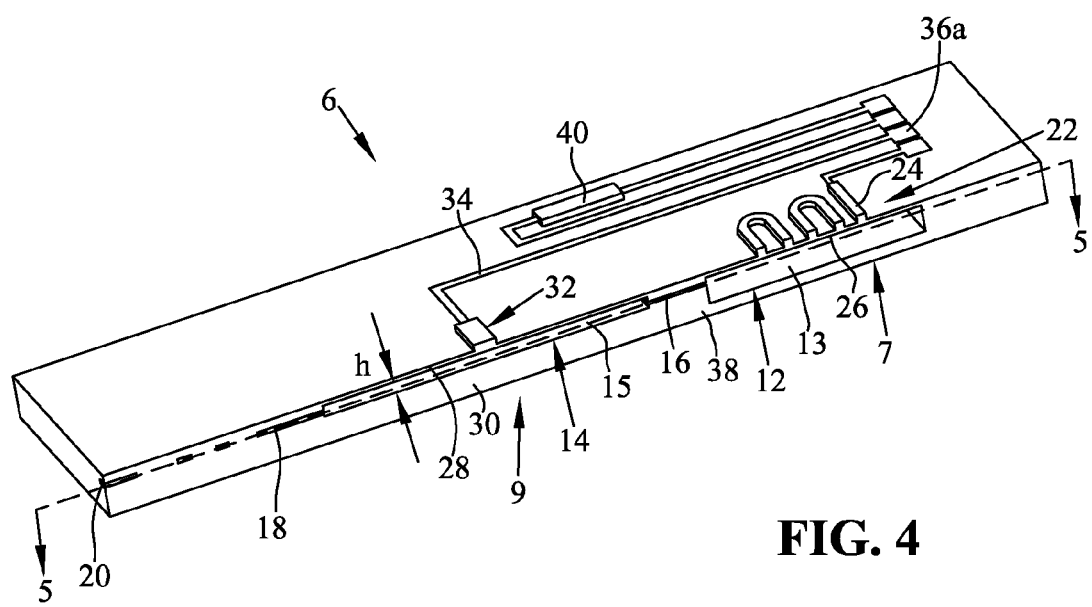
FIG. 4 is a cross-sectional view along lines IV-IV of the sensor element of FIG. 3.
Figure 5:
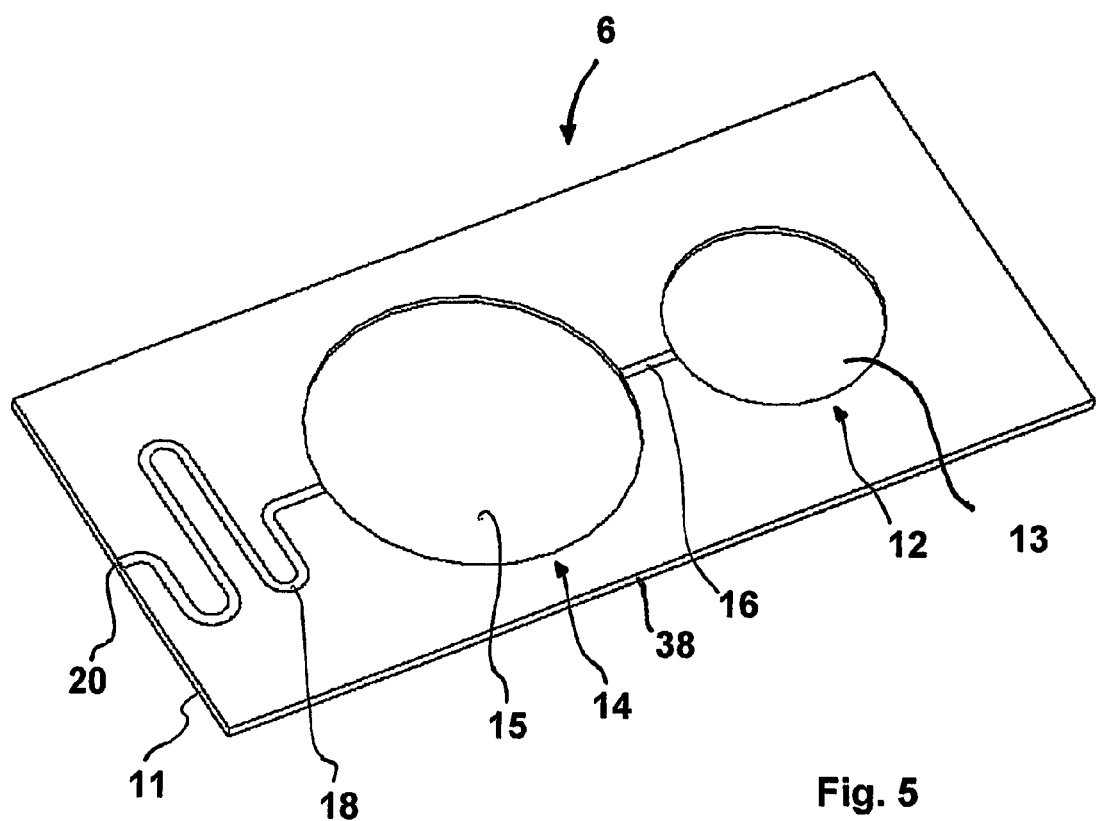
FIG. 5 is a cross-sectional view through lines V-V of the sensor element shown in FIG. 4.

Referring to FIGS. 3 to 5, the sensor element 6 comprises a gas expansion chamber 12 and a measuring chamber 14 interconnected thereto via a gas communication channel 16, an inlet orifice 18 interconnecting the measuring cavity 14 with a gas supply inlet 20, through which a supply of fresh gas flowing in the gas supply pipe enters and exits the measuring chamber.

The sensor element further comprises a heating system 22 designed to heat the gas in the expansion chamber 12. In the embodiment shown, the heating system advantageously comprises a heating resistor in form of a resistive conducting track 24 deposited or otherwise formed on a wall portion 26 bounding the cavity 13 of the expansion chamber. The resistive conducting track 24 is particularly cost-effective to manufacture, particularly with the preferred technology for producing the sensor element that will be discussed further on. It is however possible to provide the heating system with other heating elements, such as a resistive wire positioned in the cavity 13 of the expansion chamber, an induction heater or other heating means using known principles.

The measuring chamber 14 comprises a cavity 15, a membrane 28 bounding a side of the cavity 15, a membrane displacement sensor 32, and a heat sink 30 opposite the membrane 28 on the other side of the cavity 15. The membrane displacement sensor in the embodiment shown is advantageously in the form of an electrical resistor, for example a hot spot resistor 32 deposited or otherwise formed on the membrane, interconnected via conducting tracks 34 to terminals 36a, 36b of the sensor element 6 for connection to the signal processing circuit.

The electrical resistance value of the hot spot resistor 32 depends on its temperature. Electrical current supplied from the signal processing circuit flowing through the hot spot resistor 32 causes the hot spot resistor to heat up to a certain temperature. This temperature will depend on the amount of heat that is dissipated through conduction and radiation. The membrane 28, which is in this embodiment integrally formed with a substrate 38 of the sensor element 6, is made of a material with poor thermal conductivity, preferably a ceramic material. By having a very thin-walled membrane, and a measuring cavity 15 with a very small distance (h), separating the membrane from the opposite heat sink face 30, the heat dissipation of the hot spot resistor 32 will depend is primarily on the loss of heat between the membrane and the heat sink. This heat dissipation thus in turn depends on the distance (h) separating the membrane from the heat sink. By measuring the voltage (or current) across the hot spot resistor, and therefore between the electrical terminals 36a, 36b, the displacement of the membrane 28 with respect to the substrate 38 can be measured.

It is however possible, within the scope of this invention, to provide other means for measuring the membrane displacement, for example by positioning capacitive elements on the membrane 28 and the opposed wall portion 30 of the substrate and measuring the variation of capacitance, or by means of a piezoelectric strain gauge positioned on the membrane. The hot spot resistor is however particularly advantageous, since it can be manufactured easily and at low cost with the same technique used for producing the resistive heating track 24 of the heating system 22. The hot spot resistor 32 also provides very accurate and sensitive measurements of the membrane displacement and moreover, is reliable over time in the sense that its performance does not deteriorate much with age.

The pressure variation of gas in the expansion chamber may also be performed, within the scope of this invention, by other means than heating the gas in the chamber. For example, the expansion chamber may comprise a membrane driven by capacitive effect, or by a piezo-electric effect to reduce the volume of the expansion chamber, thus increasing the gas pressure in the measuring chamber. The heating element is however particularly advantageous, since it can be manufactured easily and at low cost in combination with the membrane displacement sensor elements.

The sensor element may advantageously be manufactured using technology known as low temperature co-fired ceramic (LTCC), which is per se known and for example described in the publication "Overview of low temperature co-fired ceramics tape technology for meso-system technology (MsST)" by Gongora-Rubio et a/, in Sensors and Actuators A89 (2001) 222-241. This technology is particularly advantageous for the present invention, since it enables a very large surface membrane with a very thin wall to be integrally formed in a ceramic substrate using LTCC technology, it is possible to produce a large thin membrane separated by a very small gap from an opposed substrate surface acting as a heat sink. For example, a membrane with a diameter of between 5 and 20 mm, a thickness of 40μ, and separated by a gap (h) between 10μ and 50 μm from the opposed heat sink may be made. Even though the membrane is integrally formed in a substrate of very rigid ceramic material, because it is so thin and has a relatively large diameter, yet is positioned very close to the heat sink, the displacement thereof due to very small pressure changes may be very accurately determined with a simple hot spot resistor placed on the membrane.

The sensor element 6 may be further provided with a reference resistor 40 positioned on the substrate of the membrane. The reference resistor operates essentially under steady-state conditions and provides a reference value for calibrating the signals from the measuring hot spot resistor 32.

The sensor element functions very generally as follows.

The heating system 24 is switched on and off intermittently, for example switched on for half a second, and switched off for half a second. The time on and the time off may be determined empirically as a function of the thermal constants and other material properties, dimensions and other factors. When the heating system is on, gas in the heating chamber expands, thus increasing the pressure of the gas in the measuring chamber 14, since the chambers 12, 14 communicate by way of the communication channel 16.

The inlet-outlet channel 18 is a long thin channel that acts as a resistance for the inflow and outflow of gas therethrough. The inlet-outlet channel 18 may be provided with a meander or other shapes to give it a sufficient length in a compact area.

The inlet-outlet channel 18 acts as a capillary channel with a gas flow-through resistance optimized for the pressure variations and time-constants of the measuring cycle.

Figure 6:
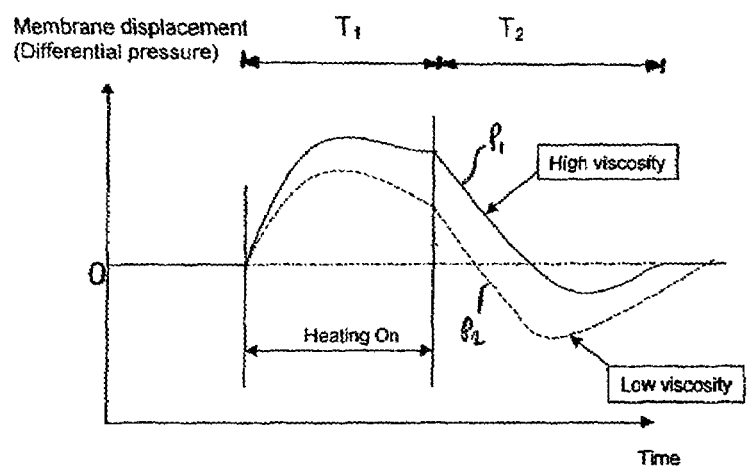
FIG. 6 is a graph illustrating the time-dependent motion of a membrane of the sensor element.

FIG. 6 is a graph illustrating the variation of the pressure in the measuring chamber as a function of time. When the heating system is on, the pressure increases as shown by the heating cycle portion T1, and when the heater is switched off, the pressure initially decreases (portion T2) due to the exit of gas through the capillary channel 18, in conjunction with a certain cooling of the gas. It may be noted that during the cooling cycle T2, a negative differential pressure is experienced, the reason being that relatively warm gas is initially expelled, but as it cools it contracts, thus leading to a negative pressure.

Figure 1:
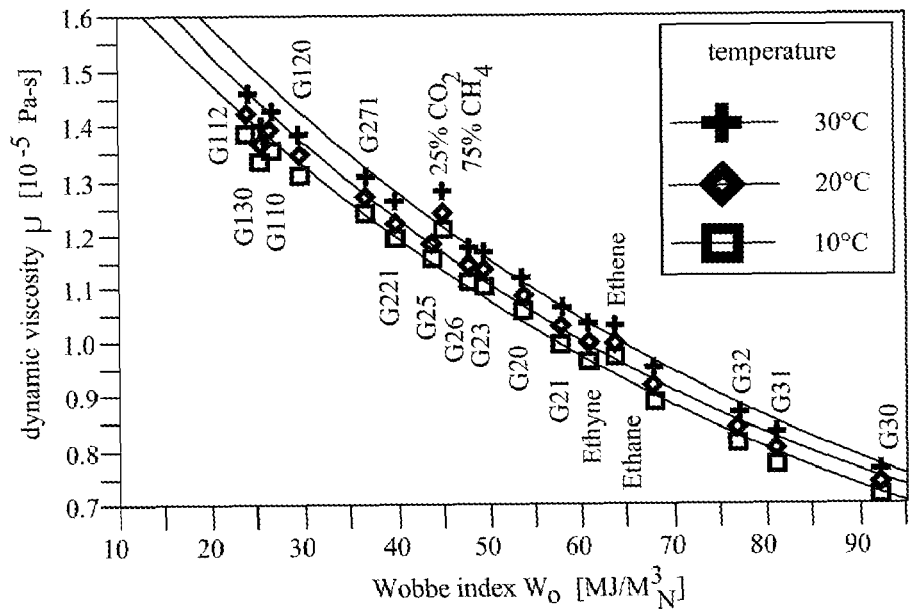
FIG. 1 is a known graph showing the relationship between the dynamic viscosity of various natural gases in relation to the Wobbe index.

The pressure profile of the cooling cycle portion T2 depends on the viscosity of the gas, as illustrated in FIG. 6, where it can be seen that the value of the differential pressure decreases as the viscosity of the gas decreases. The pressure profile ($P_1$, $P_2$) which is obtained from measurement of the membrane displacement, can be correlated with a gas viscosity, which in turn may be correlated to the Wobbe index (as illustrated in the graph of FIG. 1). Viscosity values are thus obtained by measuring the voltage across the hot spot resistor (which corresponds to the membrane displacement) and matching the time-dependent voltage profile with profiles corresponding to viscosity values, obtained empirically and stored in the signal processing system.

The cavities 13, 15 and the channels 16, 18 may be formed in the ceramic substrate using known LTCC technology, for example, by providing a carbon layer in the substrate with the shapes of the respective cavities and channels, the carbon layer being burnt away in an oxygen-rich atmosphere in a subsequent firing stage of the ceramic, as is known in the art. The LTCC technology is particularly advantageous for use in the present invention in view of the ability to integrate complex channels, cavities and other three-dimensional structures in a ceramic substrate with a high precision and with an efficient low-cost manufacturing process. A hot spot resistor and conductive tracks can also be integrated in the substrate with the LTCC technology. A particularly compact, reliable and cost-effective gas viscosity sensor can thus be achieved. The very simple and reliable means of determining membrane displacement by measuring the resistance (voltage) across a hot spot resistor on the membrane, is also very advantageous.

It may be noted that the measuring and expansion chambers may have different shapes, sizes, and positions with respect to each other without departing from the scope of this invention. For example, the measuring and expansion chambers may be stacked one on the other rather than side by side and the inlet-outlet channel may have different lengths and many other shapes, the important characteristic being that it provides a certain resistance to the flow of gas, such resistance being a function of the gas viscosity. While LTCC technology is the preferred technology for making the sensor element, it may also be made by other manufacturing techniques, for example out of multiple layers that are bonded or otherwise assembled together.

The invention claimed is:

1. Gas viscosity sensor comprising:
   a signal processing circuit and a sensor element including a gas pressure generating system and a differential pressure measuring system in fluid communication therewith, the differential pressure measuring system comprising;
   a measuring chamber bounded by a thin membrane,
   a displacement sensor adapted to measure a time dependent displacement of the membrane due to pressure variations in the measuring cavity, and
   an inlet-outlet channel or orifice interconnecting the measuring chamber to a source of gas for which viscosity is to be determined,
   wherein the inlet-outlet channel or orifice is dimensioned to provide resistance to outflow and inflow of gas in the measuring chamber,
   the membrane displacement sensor comprises a heat sensitive sensor positioned on the thin membrane, and opposed thereto a heat sink, and
   the signal processing circuit is adapted to process the measured time-dependent displacement in order to obtain a parameter dependent on the viscosity of the gas.

2. Sensor according claim 1, wherein the sensor element comprises a heat sensitive resistor on a substrate of the sensor element, operating as a reference for a heat sensitive resistor of the membrane displacement sensor.

3. Sensor according to claim 1, wherein the sensor is configured to measure a Wobbe index $W_o$ of a combustible gas by correlating the Wobbe index with a dynamic viscosity value obtained from measurement of the time dependent membrane displacement.

4. Sensor according to claim 1, wherein the signal processing circuit comprises a memory storing a set of values related to time dependent membrane displacement profiles for comparison with the time dependent displacement of the membrane.

5. Sensor according to claim 4, wherein the signal processing circuit is adapted to switch on the heating element for a duration $T_1$ corresponding to a heating cycle, and to switch off the heating element for a duration $T_2$ corresponding to a cooling cycle, and wherein the membrane displacement sensor measures the time dependent displacement of the membrane over the cooling cycle and matches or compares such profile with the values stored in the memory of the signal processing circuit.

6. Sensor according to claim 1, wherein the gas pressure generating system includes an expansion chamber separate from the measurement chamber.

7. Sensor according to claim 6, wherein the measuring chamber and expansion chamber are arranged adjacent each other in substantially a same plane and are in fluid communication via a channel.

8. Sensor according to claim 6, wherein the expansion chamber comprises a heating element arranged to heat gas in the expansion chamber.

9. Sensor according to claim 8, wherein the heating element comprises a conductive resistor track on a membrane bounding a cavity of the expansion chamber.

10. Sensor according to claim 6,wherein the measuring chamber, thin membrane, inlet-outlet channel or orifice, and expansion chamber of the pressure generating system are integrally formed in a substrate.

11. Sensor according to claim 10, wherein the substrate is a ceramic.

12. Sensor according to claim 11, wherein the sensor element is made from Low Temperature Cofired Ceramic (LTCC) tape, the chambers and orifices formed with a sacrificial layer, such as carbon black.

13. Gas viscosity sensor comprising
   a signal processing circuit and a sensor element including a gas pressure generating system and a differential pressure measuring system in fluid communication therewith, the differential pressure measuring system comprising a measuring chamber bounded by a thin membrane, a displacement sensor adapted to measure a time dependent displacement of the membrane due to pressure variations in the measuring cavity, and an inlet-outlet channel or orifice interconnecting the measuring chamber to a source of gas for which viscosity is to be determined, wherein the inlet-outlet channel or orifice having dimensions adapted to provide resistance to an outflow and inflow of gas in the measuring chamber, the pressure generating system includes an expansion chamber separate from the measurement chamber; and the signal processing circuit is adapted to process the measured time-dependent displacement to obtain a parameter dependent on the viscosity of the gas.

14. Sensor according to claim 13, wherein the measuring chamber and expansion chamber are arranged adjacent each other in substantially a same plane and are in fluid communication via a channel.

15. Sensor according to claim 13, wherein the sensor is configured to measure a Wobbe index $W_o$ of a combustible gas by correlating the Wobbe index with a dynamic viscosity value obtained from measurement of the time dependent membrane displacement.

16. Sensor according claim 13, wherein the signal processing circuit comprises a memory storing a set of values related to time dependent membrane displacement profiles for comparison with the time dependent displacement of the membrane.

17. Sensor according to claim 16, wherein the signal processing circuit is adapted to switch on the heating element for a duration $T_1$ corresponding to a heating cycle, and to switch off the heating element for a duration $T_2$ corresponding to a cooling cycle, and wherein the membrane displacement sensor measures the time dependent displacement of the membrane over the cooling cycle and matches or compares such profile with the values stored in the memory of the signal processing circuit.

18. Sensor according to claim 13, wherein the measuring chamber, thin membrane, inlet-outlet channel or orifice, and expansion chamber of the pressure generating system are integrally formed in a substrate.

19. Sensor according to claim 18, wherein the substrate is a ceramic.

20. Sensor according to claim 19, wherein the sensor element is made from Low Temperature Cofired Ceramic LTCC tape, the chambers and orifices formed with a sacrificial layer, such as carbon black.

21. Sensor according to claim 13, wherein the expansion chamber comprises a heating element arranged to heat gas in the expansion chamber.

22. Sensor according to claim 21, wherein the heating element comprises a conductive resistor track on a membrane bounding a cavity of the expansion chamber.

* * * * *